United States Patent [19]
Schiff

[11] Patent Number: 5,383,913
[45] Date of Patent: Jan. 24, 1995

[54] BIDIRECTIONAL LEAD CONNECTOR FOR LEFT OR RIGHT SIDED IMPLANTATION OF PACEMAKERS AND/OR OTHER IMPLANTABLE ELECTROPHYSIOLOGIC DEVICES AND A METHOD FOR USING THE SAME

[76] Inventor: Steven M. Schiff, 279 St. Joseph Ave., Long Beach, Calif. 90803

[21] Appl. No.: 50,859

[22] Filed: Apr. 21, 1993

[51] Int. Cl.⁶ ............................................. A61N 1/375
[52] U.S. Cl. .................................................. 607/38
[58] Field of Search ................. 607/36, 37, 38, 115, 607/116, 119, 9

[56] References Cited

U.S. PATENT DOCUMENTS

| | | | |
|---|---|---|---|
| 4,466,441 | 8/1984 | Skubitz et al. | 607/115 |
| 4,469,104 | 9/1984 | Peers-Trevarton | 607/37 X |
| 5,107,836 | 4/1992 | Fenster | 607/36 |
| 5,176,136 | 1/1993 | Giele | 607/37 |

FOREIGN PATENT DOCUMENTS

| | | | |
|---|---|---|---|
| 0102201 | 3/1984 | European Pat. Off. | 607/37 |
| 0148300 | 5/1981 | German Dem. Rep. | 607/37 |
| 2720062 | 11/1978 | Germany | 607/36 |

Primary Examiner—Angela D. Sykes
Assistant Examiner—Jeffrey R. Jastrzab
Attorney, Agent, or Firm—Beehler & Pavitt; Daniel L. Dawes

[57] ABSTRACT

A connector head for an electrophysiologic device is provided with an electrical connector which is symmetric and can be accessed by the leads either from the left or right side of the device without turning over the body of the device thereby keeping a preferred side face in a fixed relative orientation to the patient into whom the device is implanted. The purpose is to allow the smooth coiling of the excess length of the lead within the subcutaneous pocket created for the device. The connector head employs a symmetric electrical connector, which has left and right socket openings into which the plug may be inserted. Both straight through connectors in which the left and right socket openings lie along a common line, or angled left and right socket openings are provided. The angled connector head sockets form a V with respect to each other.

19 Claims, 3 Drawing Sheets

(BIPOLAR)

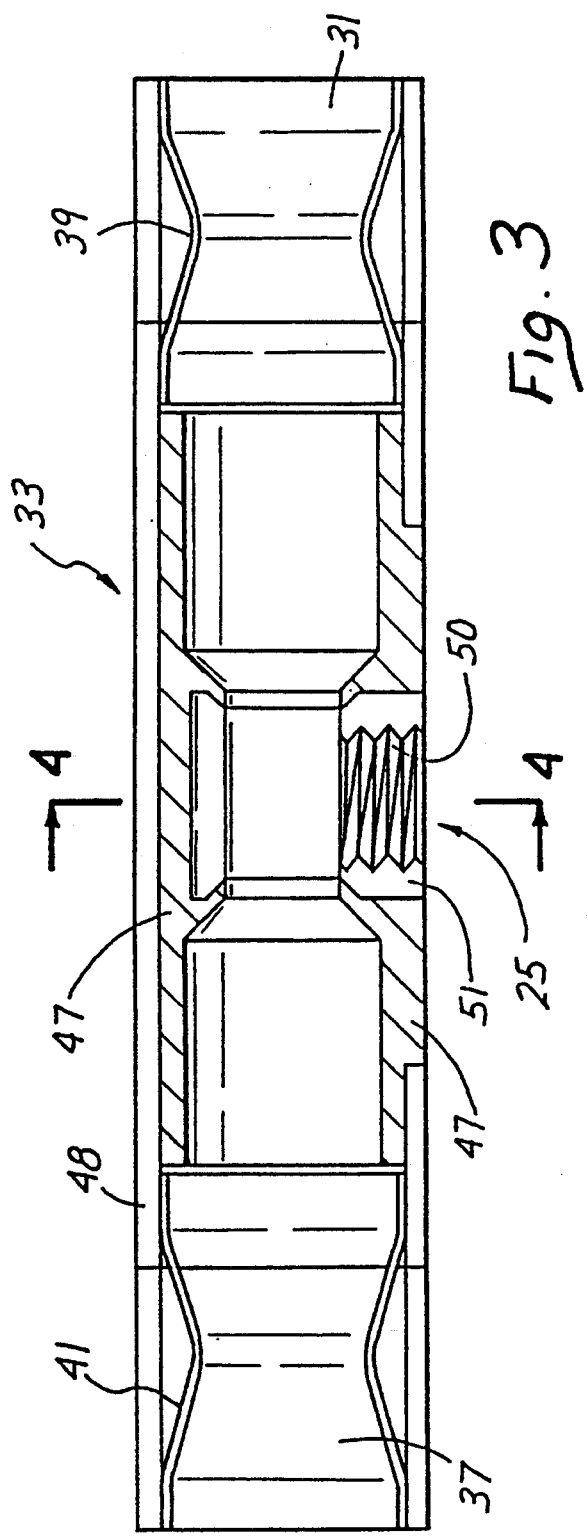
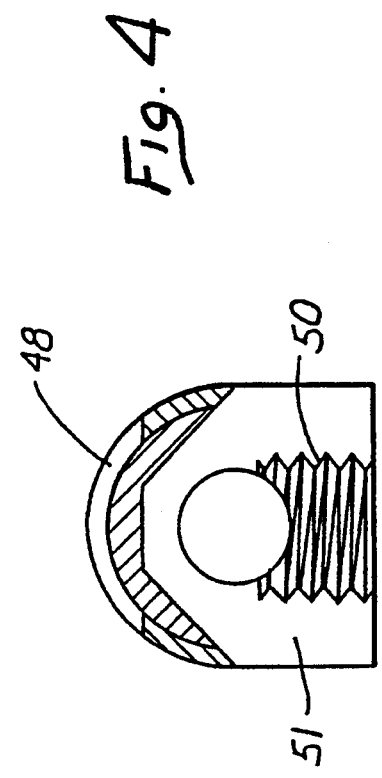

(UNIPOLAR)

BIDIRECTIONAL LEAD CONNECTOR FOR LEFT OR RIGHT SIDED IMPLANTATION OF PACEMAKERS AND/OR OTHER IMPLANTABLE ELECTROPHYSIOLOGIC DEVICES AND A METHOD FOR USING THE SAME

BACKGROUND OF THE INVENTION

1. Field of the Invention

The invention relates to the field of pacemakers and implantable electrophysiologic devices and in particular for connector heads used in pacemakers and to which the pacemaker leads connect.

2. Description of the Prior Art

Permanent implantable pacemakers are bioelectrical devices designed to monitor and maintain heart rates of patients with episodically or chronically slow or fast heart rates which produce significant symptoms. In general, the pacemakers are set to provide minimum and maximum heart rates and, through their sensing or monitoring capabilities, are designed to function on demand from sensed heart signals based upon signal analysis provided by programs stored within the pacemaker.

Pacemakers are comprised of two basic components, namely a pulse generator contained within a casing, which is subcutaneously implanted, and leads which extend from the pulse generator into the heart chamber through the veins. The pulse generator is the more complex of the two components. It is a hermetically sealed unit which is surgically implanted into a pocket created under the skin and subcutaneous fat below the clavicle on either the right or left side of the upper chest. The pulse generator contains a battery, and microprocessor that regulates the output of the pacemaker to the heart. Frequently, external communication with the pacemaker is possible by means of radio telemetry both to inquire as to the mode or the function of the pulse generator, and when necessary to reprogram that parameter. The most complex pacemakers have multiple programs with two leads disposed into two separate chambers in the heart, which programs can be selected to control the pulse generator's output.

The leads function as the electrical pathways between the pulse generator and the selected area of the heart muscle. They are most often inserted from the surgical pocket defined under the skin for the generator unit into the subclavian vein which runs to the heart. The leads are placed in a stable position within a cardiac chamber using X-ray visualization. Impulses travel in both directions over the lead to allow the pulse generator to both sense and pace the appropriate cardiac chamber or muscle tissue at the appropriate time.

The leads are generally defined as either unipolar or bipolar. A unipolar lead is a lead having one electrode, the cathode, at its distal tip. The other electrode, the anode, is comprised of the metallic casing of the hermetically sealed unit, the pulse generator. The proximal end of the unipolar lead, which connects to the pulse generator, has a single electrical contact for the cathode. Bipolar leads are defined to have both the cathode and anode at or near the distal end of the lead within the heart chamber with the cathode being the most distal. There are two electrical contacts at the proximal end of the lead connected to the pulse generator, one for the cathode and one for the anode.

Many pacemakers are now constructed or designed to be connected to bipolar leads. However, the pulse generators may be set to function either in a unipolar or bipolar mode because there are advantages and disadvantages to each. It is not uncommon to switch the mode of operation of the pacemaker from one to the other depending upon the clinical needs of the patient and the problems encountered in the function of the pacemaker in question. In addition, dedicated unipolar pacemakers connected to unipolar leads continue to be manufactured and implanted.

A specific issue with respect to the function of the unipolar pacing modes is a concern that the pulse generator might sense the electrical activity of muscles within the chest wall, such as the pectoral muscle. If this electrophysiological activity originating from the muscles is interpreted by the pacemaker as cardioactivity, the pacemaker program may shut off the output of the pulse generator. If the patient is pacemaker dependent, this in turn may cause him to lose consciousness or worse.

For this reason, only one side of the pulse generator's casing is used to function as an electrode or anode in unipolar pacing. As consequence of this fact, the hermetically sealed unit in which the pulse generator is encased must always be implanted with its anode side facing anteriorly or away from the underlying chest wall muscles. Even if the unit is implanted with the initial intention of functioning as a bipolar pacemaker, its orientation within the chest pocket must always be fixed, since it may become necessary to reprogram the unit to function in the unipolar mode at some time in the future.

Recently by agreement among pacemaker manufacturers, all pacemaker leads are designed according to a uniform specification designated as IS-1 or VS-1 to allow every company's leads to be interchangeable with every other company's pulse generator connector head. The connector head is the portion of the pulse generator to which the leads are electrically and physically connected. The leads are manufactured to a fixed length which cannot be adjusted by the surgeon in the operating room. The leads are always long enough to allow the appropriate cardiac chamber to be reached with some excess lead being provided. The excess length is then coiled into a loop around the pulse generator. The pulse generator with its coil of excess lead is then placed into the subcutaneous pocket created by the surgeon, and the skin is sutured closed.

Turn to FIG. 1 wherein a bipolar pacemaker of the prior art is depicted in plan view. Pacemaker 10 includes a connector head 12 to which a lead 14 is to be connected. Prior art pacemakers 10 have a specific physical configuration such as shown in FIG. 1. When viewed from the anode side of casing 16, which is usually the side of pacemaker 10 with the manufacturer's name or logo on it, connector head 12 at the top of pacemaker 10 is positioned such that lead 14 must be connected into connector head 12 only from the right side as seen in the configuration in FIG. 1. When lead 14 extends from the right side of connector head 12, its natural tendency is to coil in a clockwise direction around pulse generator 10. Such a configuration allows a smooth entry of the lead 14 into the subclavian vein via a surgical pocket on the right side of the chest. In some cases, it is medically advantageous to have the pacemaker on the left side of the chest either because of various aspects of the patient's anatomy or because of previous surgery involving the chest wall.

In FIG. 6 wherein a unipolar of the prior art is depicted in plan view a similar configuration to FIG. 1 occurs. Lead 82 must be connected into connector head 70 of pacemaker 10 only from the right side as seen in FIG. 6.

Returning to FIG. 1, attempts to place pacemaker 10 on the left side of the chest poses significant problems in coiling the excess length of lead 14 into the surgical pocket. A lead entering the left subclavian vein is most easily coiled around pacemaker 10 with a connector head which allows the leads to emerge from the left side of pacemaker unit 10. However, pacemaker 10 cannot be turned over to permit left side exit of lead 14 from connector head 10 because the anode side of the casing must be kept away from the underlying muscle.

Therefore, the surgeon must use pacemaker 10 in the configuration as shown in FIG. 1 even when implanted on the left side. This adds significant time in surgery and may require some enlargement or modification of the pocket. In some cases, the entire assembly of pacemaker 10 and lead 14 assumes an awkward lie or configuration within the surgical pocket with a knuckle or loop of lead 14 protruding into a corner of the pocket. Such a lead knuckle or kink may cause patient discomfort or subcutaneous protrusions which are unwanted and may lead to reoperation. The problem with the left side implantation becomes even more exacerbated in the case where the patient is to receive a pacemaker 10 having dual leads.

What is needed is a design for a connector head which will facilitate the actual surgical implantation of the entire pacemaker generator and its leads within the operating theater in either the left or right side of the patient's chest. What is needed is a pacemaker configuration which avoids each of these problems but still allows the pacemaker to be always disposed within the surgical pocket anode side up.

BRIEF SUMMARY OF THE INVENTION

The invention is an improvement in a pacemaker having a connector head for use in combination with pacemaking leads and having a casing coupled to the connector head. The improvement comprises a bidirectional electrical connector disposed within the connector head to accept insertion of the leads from either one of at least two directions and to make electrical contact with the lead when inserted within the connector in either of the two directions. As a result, the pacemaker may be implanted within a patient on either the left or right side of the patient with equal ease.

The invention is described in both unipolar and bipolar configurations with the common objective of both configurations being access to the electrical contacts within the pacemaker connector head from either the left or right side.

The leads are provided with an end plug having one, two or more electrodes defined thereon. The connector comprises corresponding contacts arranged and configured within the connector to electrically couple with the electrodes on the plug when the plug is fully inserted within the connector.

In the bipolar configuration the connector comprises a left lateral contact and a right lateral contact. The left and right lateral contacts are electrically coupled together to function as one electrical contact assembly for the anode within the connector. The electrical contacts are accessible from either the left or right side of the pacemaker. A common central contact is disposed between the left and right lateral contacts to function as a second electrical contact for the cathode within the connector.

In the unipolar configuration the connector comprises a common central contact, which is accessible from either the left or right side of the pacemaker, and which functions as an electrical contact for the cathode within the pacemaker.

In the following descriptions reference is made to both unipolar and bipolar devices. The substantive difference between the unipolar and bipolar devices is that in a bipolar device there are two electrically joined lateral contacts for the anode, and in a unipolar device there is no electrical contact for the anode, because there is no anode on the lead. In the unipolar device the front of the pulse generator casing functions as the anode.

In one embodiment the connector has a longitudinal axis defined therethrough. The longitudinal axis is defined parallel to a single line.

In another embodiment the connector is comprised of at least two inclined connector head socket portions. In the bipolar device the left lateral contact is disposed in one connector head socket portion and the right lateral contact is disposed in the other one of the connector head socket portions. The two inclined connector head sockets intersect at a common region and the central contact is disposed in the common region.

The plug is made according to a standard (IS-1 or VS-1). The connector is made to accept the standardized plug. A bipolar plug has a predefined polarity and maintains the predefined polarity when plugged into the bipolar connector regardless of whether it is plugged from the left or right side. In the setting of a dedicated unipolar lead and pacemaker, plug and contact polarity is not an issue. The ability to access the central cathode contact from either the left or right side of the pacemaker is still beneficial with respect to the smooth coiling of excess lead into the pocket, regardless of which side of the chest into which the pacemaker is implanted.

The invention is also characterized as a connector head socket for use in combination with a pacemaker body and at least one pacemaker lead terminating with a plug having one or more electrodes. The invention comprises a body, a left end socket opening defined in the body, and a right end socket opening defined in the body. In the bipolar configuration, the lateral contacts are disposed in the left end socket opening and the right end socket opening for providing electrical contact with the body electrode, anode, of the plug when the plug is inserted through the left or right end socket opening. A central contact is disposed within the body for receiving the end electrode, cathode, of the plug when the plug is disposed either through the left or right end socket opening and fully seated therein. As a result, electrical coupling of bipolar leads to the connector head may be made either on the left or right sides with equal facility and without affecting lead polarity.

The left and fight end socket openings are symmetrical one with respect to the other to define a center of symmetry. The central contact element for receiving the end electrode on the plug is disposed at the center of symmetry of the left and right end socket openings in both unipolar and bipolar devices.

In the bipolar configuration, the lateral contact further comprises a metallic body extending between the left to the fight contact to provide electrical connection therebetween and to provide structural definition for the connector head.

The invention is also characterized as a method for providing ambidextrous contact of leads to a pacemaker comprising the steps of providing the pacemaker with a symmetric connector head to facilitate implantation into a surgical pocket in a patient. The symmetric connector head has an electrical contact defined therein which is accessible from a left side or right side of the connector head. The connector head is accessed from one of the left or right sides of the connector head with a plug provided on the proximal end of the lead. Excess length of the lead is coiled around the pacemaker in either a clockwise or counterclockwise direction as determined by the direction of the plug as the plug extends from the connector head, so that the lead is coiled within a surgical pocket provided around the pacemaker without reversing the clockwise or counterclockwise sense of coiling of the lead.

The method further comprises the step of sealing an opposing end of the socket opening within the connector head, which opposing socket opening is the unused socket opening, so that integrity of electrical connection within the connector is maintained. The method further comprises the step of accessing the connector head with multiple leads and performing the step of coiling with each of the leads.

The invention may now be better visualized by turning to following drawings wherein like elements are referenced by like numerals.

BRIEF DESCRIPTION OF THE DRAWINGS

FIG. 3 is a side cross sectional view of one embodiment for the connector head socket diagrammatically depicted in FIG. 2.

FIG. 4 is a perpendicular cross sectional view of the connector head socket of FIG. 3 as seen through sectional lines 4—4 of FIG. 3.

The invention and its various embodiments may now be better understood by turning to the following detailed description.

DETAILED DESCRIPTION OF THE PREFERRED EMBODIMENTS

A connector head for a cardiac electrophysiologic device is provided with an electrical connector which is symmetric and can be accessed by the leads either from the left or right side of the device without turning over the device body, thereby keeping a preferred side face in a fixed relative orientation to the patient into whom the pacemaker is implanted. A cardiac electrophysiologic device is defined to include pacemakers, implantable defribrillators, and any other type of device for affecting or monitoring cardiac electrophysiologic function. The invention also includes any other implantable electrophysiologic devices such as neural simulators.

In the bipolar configuration the connector head employs a symmetric electrical connector, which has left and right socket openings into which the plug may be inserted. Each left and right socket opening has a contact arranged and configured to make electrical connection with a lateral electrode, the anode, provided on the plug. The electrode tip on the plug is inserted into either the left or right socket and comes to rest at a central point of symmetry where a central electrical contact is provided. The central contact makes electrical contact with the tip electrode of the plug, the cathode. The contacts disposed in either the left or right end socket openings are electrically coupled in common so that only two wires are coupled from the connector head into the casing for appropriate electrical connections for the anode and cathode within device in a conventional manner. Both straight through connectors in which the left and right socket openings lie along a common line, or angled left and right socket openings are provided. The angled connector head sockets form a V with respect to each other and the central contact, the cathode, is disposed at the apex of the V.

In the unipolar configuration there are no lateral electrodes on the plug and no lateral anode contacts within the connector head. The design of the connector head and socket is otherwise identical to the bipolar design, allowing the electrode tip on the plug to be inserted into either the left or right socket opening and to come to rest at a central point of symmetry where a central electrical contact for the cathode is provided.

Figure 1:
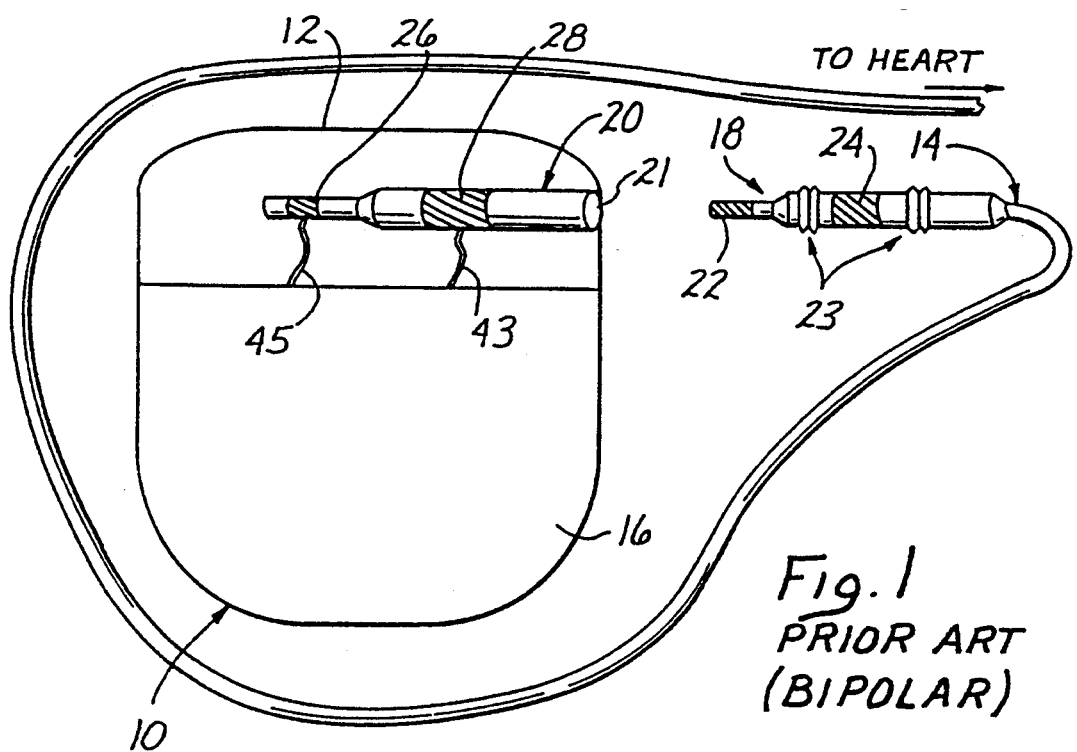
FIG. 1 is a diagrammatic side view of a bipolar pacemaker and lead having a connector head as used in the prior art.

The prior art bipolar pacemaker of FIG. 1 diagrammatically shows a connector head 12 in which a bipolar plug 18 of lead 14 is to be inserted within a connector head socket 20 within connector head 12. Plug 18 includes a tip cathode 22 and body anode 24. Plug 18, when plugged into opening 21 of connector head socket 20, makes electrical contact between tip cathode 22 and a cathode contact 26 defined within connector head socket 20. Similarly, body anode 24 of plug 18 electrically contacts anode contact 28 within connector head socket 20. Contacts 26 and 28 then are electrically wired through conventional means diagrammatically represented by anode wire 43 and cathode wire 45 to appropriate circuitry within pacemaker 10 contained with casing 16. The particular circuitry of the pacemaker is not material to the details of the invention and therefore will not be further described. Plug 18 also includes a number of additional conventional structural details, such as sealing rings 23, which provide for sealing of plug 18 within connector head socket 20 to prevent blood and body fluids from entering connector head socket 20 or otherwise interfering with the electrical contact made between plug 18 and connector head 20.

Figure 2:
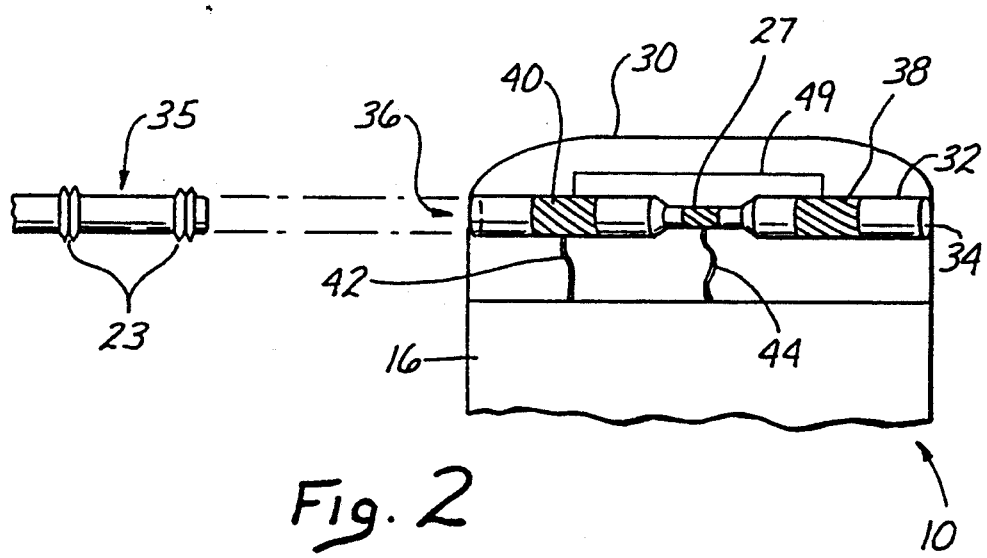
FIG. 2 is a diagrammatic side view of the upper portion of a bipolar pacemaker and connector head devised according to the invention. It is shown with the inert plug for sealing an open end.

Turn now to FIG. 2 wherein a diagrammatic side view of a bipolar connector head 30 of the invention is shown. The same plug 18 of FIG. 1, as used in the prior art, is used in combination with the improved connector head 30 of the invention. In the embodiment of FIG. 2, connector head 30 includes a connector head socket 32 which is bidirectional or symmetric thereby permitting insertion of plug 18 into either a right end opening 34 or left end opening 36 of connector head socket 32. As shown in FIG. 2, the right portion of connector head socket 32 includes an anode contact 38 which is electrically coupled by wire 49 to an anode contact 40 similarly provided in the left portion of connector head 30. Contacts 38 and 40 are similarly coupled through a wire 42 to the appropriate connection or circuitry within casing 16.

Cathode contact 27 is provided within the middle of connector head socket 32 and is shared in common between the left and right portions of connector head socket 32. Cathode contact 27 is coupled through wire 44 to appropriate circuitry within casing 16.

As can be appreciated by viewing the diagrammatic depiction of FIG. 2, connector head 12 is substantially symmetrical and is comprised of three contacts. A pulse generator used with a single chamber of the heart would therefore have three contacts and a dual chamber device would have six. It is within the scope of the invention that the exact configuration of the contacts within head 30 will conform with the standard IS-1 or VS-1 lead connector ends, or other such standards for lead configurations which may be adopted from time to time.

Lateral anode contacts 38 and 40 are electrically coupled to each other by wire 49, but isolated electrically from center contact 27. Lateral contacts 38 and 40 couple with ring connector 24 on plug 18 in the standard IS-1 or VS-1 lead and in a bipolar program mode function as the anode. Plug 18 may therefore be placed either in the left or right hand side of connector head 30 while still maintaining the appropriate polarity of the cathode and anode on the lead. When plug 18 is inserted into open end 34, the remaining open end 36 of connector head socket 32 is provided with a plug 35 which is electrically inert and which is designed with sealing rings 23 to prevent leakage of current between anode contact 40 and cathode contact 27 and to prevent leakage of current from connector head socket 32, or the invasion of any bodily fluids within the connector head socket. Inert plug 35 has a similar form to plug 18 for providing sealing, but without the electrodes or electrode supporting structure. No modification of the circuitry or casing 16 is required in order to be adapted to connector head 30 of the present invention.

FIG. 3 is a side cross sectional view of one implementation of socket 32 of bipolar connector head 30, shown diagrammatically in FIG. 2, and FIG. 4 is a perpendicular cross sectional view taken through section lines 4—4 of FIG. 3. In FIG. 3 connector socket 33 is comprised of a plastic or insulating body 47 disposed within a metallic sleeve 48. Right end 31 includes anode spring contact 39 resiliently fixed against the right end of sleeve 48. Similarly, left end 37 is provided with anode spring contact 41 resiliently retained within the left end portion of sleeve 48. Electrical coupling between contacts 39 and 41 is provided by means of the conductivity of sleeve 48. Center electrode 25 is provided in the form of a screw pin assembly 51 which has a threaded bore 50 defined therein to receive a threaded pin (not shown) to provide a secure attachment of a plug, such as plug 18 of FIG. 1, into connector head socket 33. Although FIG. 3 shows a spring and resilient contact, any and all means now known or later devised for making secure electrical contact may be substituted.

Figure 5:
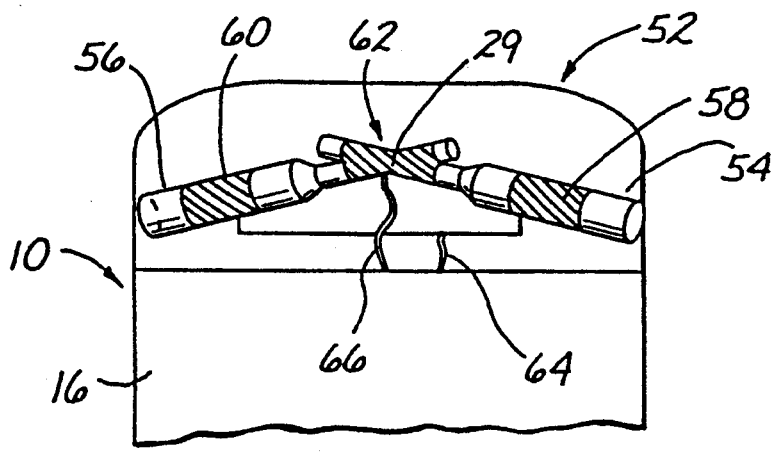
FIG. 5 is a diagrammatic side view of the upper portion of an alternative embodiment of the bipolar connector head according to the invention, the teachings of which can be extended to the unipolar embodiment shown in FIG. 7.

FIG. 5 is a diagrammatic side view of an alternative embodiment of the invention wherein a bipolar connector head 52 is provided with two angled intersecting connector head sockets 54 and 56. Connector head sockets 54 and 56 are generally cylindrical but each is canted in order to incline plug 18 as it extends from connector head sockets 54 and 56 so that lead 14 can be more easily wrapped in clockwise or counterclockwise direction around casing 16 respectively. Each connector head socket 54 and 56 is provided with lateral or proximate electrical contacts 58 and 60 respectively which are electrically coupled together and then connected to the anode terminal within pacemaker 10 by wire 64. However, where connector head sockets 54 and 56 intersect in central region 62, central connector 29 is provided to function as the cathode terminal, which is connected to the cathode terminal within pacemaker 10 by wire 66.

The embodiment of FIG. 5 has two advantages, first it provides for an easier wrap in each direction around pacemaker 10. Second, a smaller or narrower connector head 52 can be provided while still accommodating the same standardized length of plugs complying with IS-1 of VS-1 standards.

Figure 6:
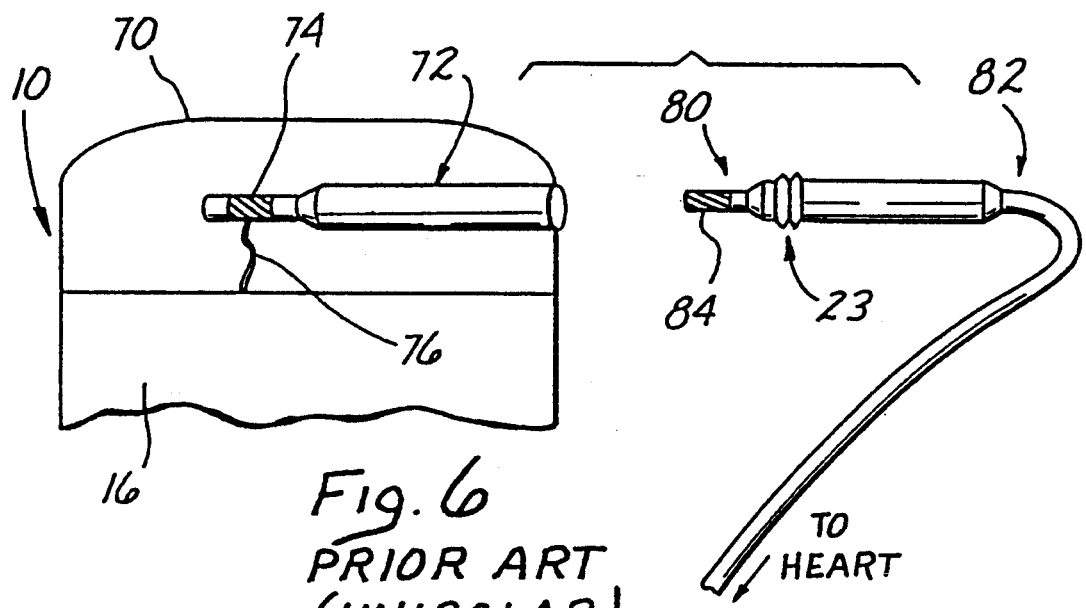
FIG. 6 is a diagrammatic side view of the upper portion of a unipolar pacemaker and lead having a connector head as used in the prior art.

A similar though electrically simpler design for a bidirectional unipolar embodiment of the invention is now described. Turn to FIG. 6 wherein a diagrammatic side view of a prior art unipolar connector head 70 is shown. Unipolar plug 80 of lead 82 is to be inserted into connector head socket 72. Tip cathode 84 comes to rest and makes electrical contact at cathode contact 74. Contact 74 is electrically wired through conventional means, diagrammatically represented by cathode wire 76 to appropriate circuitry within pacemaker 10 contained within casing 16. The front surface of casing 16 is the anode.

Figure 7:
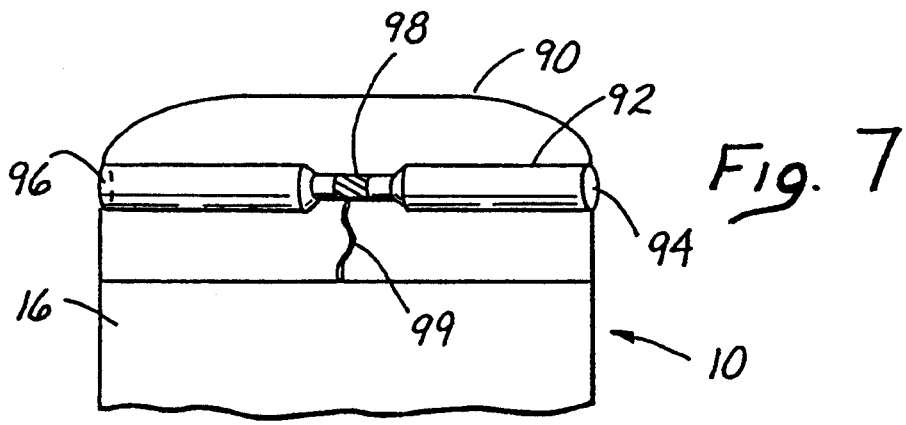
FIG. 7 is a diagrammatic side view of the upper portion of a unipolar pacemaker and connector head devised according to the invention.

Turn now to FIG. 7 wherein a diagrammatic side view of a unipolar connector head 90 of the invention is shown. The same plug 80 of FIG. 6 as used in the prior art is used in combination with the improved connector head 90 of the invention. In the embodiment of FIG. 7, the connector head 90 includes a connector head socket 92 which is bidirectional or symmetric, thereby permitting insertion of plug 80 into either a right end opening 94 or a left end opening 96 of connector head socket 92. Cathode contact for tip electrode 84 on plug 80 is provided by cathode contact 98 at the center of connector head socket 92. Cathode contact 98 is coupled by wire 99 to appropriate circuitry within casing 16.

Similar physical modifications as described for the bipolar connector socket with angulated sockets and/or multiple leads are applicable to the unipolar device.

Thus what is shown is a design for unipolar or bipolar connector heads which are equally adapted for both right sided and left sided implantations without requiring the manufacturer to make or stock pacemaker inventories having left or right handed configurations. No matter which way the lead is inserted, the surgeon may decide at the time of surgery which way to wrap the lead around the pacemaker, thereby avoiding any knuckles or awkward lie of the excess lead length within the surgical pocket, and optimizing the pocket volume or geometry in the patient.

Many alterations and modifications may be made by those having ordinary skill in the art without departing from the spirit and scope of the invention. For example, although the illustrated embodiments have been described in relation to leads having one or two electrodes, it is expressly within the scope of the invention to include more than two electrodes on the lead.

Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the germ of the invention.

I claim:

1. An improvement in an electrophysiologic device comprising:
   a connector head for use in combination with at least one plug-in type lead having;
   a casing coupled to said connector head; and
   an electrically integral bidirectional electrical connector means disposed within said connector head for reattachably inserting only one said plug-in type lead according to user selection from either one of at least two directions and to make electrical contact with said lead when inserted within said connector in either of said two directions,
   whereby said device may be implanted within a patient on either the left or right side of said patient with equal ease.

2. The improvement of claim 1 wherein said leads are provided with an end plug having at least one electrode defined thereon and wherein said connector comprises at least one corresponding contact arranged and configured within said connector to electrically couple with said electrode on said plug when said plug is fully inserted within said connector.

3. The improvement of claim 2 wherein said plug is arranged and configured according to a standard and is thus defined as a standardized plug, said connector being arranged and configured to accept said standardized plug.

4. The improvement of claim 1 wherein said plug adapted for coupling within said connector has a predefined polarity and wherein said connector maintains said predefined polarity with respect to said plug when plugged into said connector regardless of whether being plugged from said left or right side.

5. An improvement in an electrophysiologic device having a connector head for use in combination with at least one lead and having a casing coupled to said connector head, said improvement comprising:
   a bidirectional electrical connector means disposed within said connector head for accepting insertion of said lead from either one of at least two directions and to make electrical contact with said lead when inserted within said connector in either of said two directions, wherein said electrophysiologic device has a left and right side, and wherein said connector comprises:
   a left lateral contact;
   a right lateral contact, said left and right lateral contacts being electrically coupled together to function as one electrical contact assembly within said connector, which electrical contacts are accessible from either said left or right side of said electrophysiologic device; and
   a common central contact disposed between said left and right lateral contacts to function as a second electrical contact within said connector,
   whereby said device may be implanted within a patient on either the left or right side of said patient with equal ease.

6. The improvement of claim 5 wherein said connector is straight and thus has a longitudinal axis defined therethrough, said longitudinal axis being defined parallel to a single line.

7. The improvement of claim 5 wherein said connector is comprised of at least two inclined connector head socket portions, said left lateral contact being disposed in one connector head socket portion and said right lateral contact being disposed in said other one of said connector head socket portions.

8. The improvement of claim 7 wherein said two inclined connector head sockets intersect at a common region and wherein said central contact is disposed in said common region.

9. A connector head socket for use in combination with a connector head of an electrophysiologic device implanted into a patient and at least one lead terminating with a plug having an end electrode and lateral electrode comprising:
   a body of said connector head socket;
   a left end socket opening defined in a left side of said body;
   a right end socket opening defined in a right side of said body;
   lateral contact means disposed in said body adjacent to said left end socket opening and said right end socket opening for providing an user selected reattachable electrical contact with said lateral electrode of said plug when said plug is inserted through said left or right end socket opening at the time of insertion of said electrophysiologic device in said patient; and
   an electrically integral end contact means disposed within said body for receiving said end electrode of only one said plug when said plug is disposed either through said left or right end socket opening and fully seated therein,
   whereby electrical coupling of said lead to said connector head may be made either on the left or right sides of said body with equal facility.

10. The connector head of claim 9 wherein said left end socket opening and said right end socket opening are collinear with each other.

11. The connector head of claim 10 wherein said line upon which said left end socket opening is disposed and said line upon which said right end socket opening is disposed is a common line, said end contact means being disposed on said common line between said left and right end socket openings.

12. The connector head of claim 9 wherein said left end socket opening is accessible along a first direction and said right end socket opening is accessible along a second direction, said first and second directions being inclined with respect to each other and intersecting at a common point.

13. A connector head socket for use in combination with a connector head of an electrophysiologic device and at least one lead terminating with a plug having an end electrode and lateral electrode comprising:
   a body of said connector head socket;
   a left end socket opening defined in a left side of said body;

a right end socket opening defined in a right side of said body;

lateral contact means disposed in said body adjacent to said left end socket opening and said right end socket opening for providing electrical contact with said lateral electrode of said plug when said plug is inserted through said left or right end socket opening; and end contact means disposed within said body for receiving said end electrode of said plug when said plug is disposed either through said left or right end socket opening and fully seated therein, wherein said lateral contact means is comprised of a corresponding left and right contact, said left and right contact being electrically coupled together to form an electrically common contact, whereby electrical coupling of said lead to said connector head may be made either on the left or right sides of said body with equal facility.

14. The connector head of claim 13 wherein said left and right contact is a spring contact.

15. The connector head of claim 13 wherein said lateral contact means further comprises a metallic body extending between said left contact to said right contact to provide electrical connection therebetween and to provide structural reinforcement for said connector head.

16. A connector head socket for use in combination with a connector head of an electrophysiologic device and at least one lead terminating with a plug having an end electrode and lateral electrode comprising:

a body of said connector head socket;

a left end socket opening defined in a left side of said body;

a right end socket opening defined in a right side of said body;

lateral contact means disposed in said body adjacent to said left end socket opening and said right end socket opening for providing electrical contact with said lateral electrode of said plug when said plug is inserted through said left or right end socket opening; and end contact means disposed within said body for receiving said end electrode of said plug when said plug is disposed either through said left or right end socket opening and fully seated therein, wherein said left and right end socket openings are symmetrical one with respect to the other to define a center of symmetry, and wherein said end contact means is disposed at said center of symmetry of said left and right end socket openings, whereby electrical coupling of said lead to said connector head may be made either on the left or right sides of said body with equal facility.

17. A connector head socket for use in combination with a connector head of an electrophysiologic device and at least one lead terminating with a plug having an end electrode and lateral electrode comprising:

a body of said connector head socket;

a left end socket opening defined in a left side of said body;

a right end socket opening defined in a right side of said body;

lateral contact means disposed in said body adjacent to said left end socket opening and said right end socket opening for providing electrical contact with said lateral electrode of said plug when said plug is inserted through said left or right end socket opening; and end contact means disposed within said body for receiving said end electrode of said plug when said plug is disposed either through said left or right end socket opening and fully seated therein, wherein said left end socket opening is accessible along a first direction and said right end socket opening is accessible along a second direction, said first and second directions being inclined with respect to each other, and wherein said inclined left and right end socket openings intersect at a common region, said end contact means being disposed within said common region, whereby electrical coupling of said lead to said connector head may be made either on the left or right sides of said body with equal facility.

18. A method providing ambidextrous contact to an electrophysiologic device implanted into a patient comprising the steps of:

implanting said electrophysiologic device with a symmetric connector head into a surgical pocket in said patient, said symmetric connector head having an electrically integral bidirectional contact defined therein accessible from a left side or right side of said connector head;

accessing said connector head from one of said left or right sides of said connector head according to user selection with a plug provided on the proximal end of a plug-in type lead;

reattachably electrically coupling only one said plug-in type lead into said an electrically integral bidirectional connector head from either one of said left and right sides according to user selection to make electrical contact with said plug-in type lead when inserted within said connector head in either of said two directions while said electrophysiologic device is implanted into said patient; and coiling excess length of said lead around said electrophysiologic device in either a clockwise or counterclockwise direction as determined by whether said lead is plugged into said connector head on the left or right side so that said lead is coiled within a surgical pocket provided around said electrophysiologic device without reversing the clockwise or counterclockwise sense of coiling of said lead and causing a knuckle or awkward lie of said coiled lead.

19. A connector head socket for use in combination with a connector head of an electrophysiologic device for implantation into a patient and at least one lead terminating with a plug having an electrode comprising:

a body of said connector head socket;

a left end socket opening defined in a left side of said body;

a right end socket opening defined in a right side of said body; and an electrically integral contact means disposed in said body communicating with said left end socket opening and said right end socket opening for providing electrical contact with said electrode of only one said plug when said plug is reattachably plugged into said connector head according to user selection when said electrophysiologic device is implanted into said patient through said left or right end socket opening, whereby electrical coupling of said lead to said connector head may be made either on the left or right sides of said body with equal facility.

* * * * *